United States Patent
Burkoth et al.

[11] Patent Number: 5,843,468
[45] Date of Patent: *Dec. 1, 1998

[54] SKIN PERMEATION ENHANCER COMPOSITIONS COMPRISING GLYCEROL MONOLAURATE AND LAURYL ACETATE

[75] Inventors: Terry L. Burkoth, Oxford, England; Lina T. Taskovich, Palo Alto, Calif.; Russell D. Beste, Mountain View, Calif.; Robert M. Gale, Los Altos, Calif.; Eun Soo Lee, Redwood City, Calif.; Richard D. Hamlin, Newark, Calif.; Su LL Yum, Los Altos, Calif.

[73] Assignee: ALZA Corporation, Palo Alto, Calif.

[*] Notice: The term of this patent shall not extend beyond the expiration date of Pat. No. 5,785,991.

[21] Appl. No.: 644,922

[22] Filed: May 13, 1996

Related U.S. Application Data

[63] Continuation-in-part of Ser. No. 481,549, Jun. 7, 1995, Pat. No. 5,785,991.

[51] Int. Cl.$^6$ .................................. A61F 13/02
[52] U.S. Cl. ............................. 424/448; 424/449
[58] Field of Search ..................... 424/448, 449

[56] References Cited

U.S. PATENT DOCUMENTS

| | | | |
|---|---|---|---|
| 3,472,931 | 10/1969 | Stoughton et al. | 424/180 |
| 3,527,864 | 9/1970 | MacMillan et al. | 424/177 |
| 3,598,122 | 8/1971 | Zaffaroni | 128/268 |
| 3,598,123 | 8/1971 | Zaffaroni | 128/268 |
| 3,731,683 | 5/1973 | Zaffaroni | 128/268 |
| 3,797,494 | 3/1974 | Zaffaroni | 128/268 |
| 3,896,238 | 7/1975 | Smith | 424/358 |
| 3,903,256 | 9/1975 | MacMillan et al. | 424/59 |
| 3,952,099 | 4/1976 | Smith | 424/227 |
| 4,046,886 | 9/1977 | Smith | 424/227 |
| 4,130,643 | 12/1978 | Smith | 424/238 |
| 4,130,667 | 12/1978 | Smith | 424/361 |
| 4,144,317 | 3/1979 | Higuchi et al. | 424/21 |
| 4,286,592 | 9/1981 | Chandrasekaran | 128/260 |
| 4,299,826 | 11/1981 | Luedders | 424/181 |
| 4,314,557 | 2/1982 | Chandrasekaran | 128/260 |
| 4,335,115 | 6/1982 | Thompson et al. | 424/181 |
| 4,343,798 | 8/1982 | Fawzi | 424/240 |
| 4,379,454 | 4/1983 | Campbell et al. | 604/897 |
| 4,405,616 | 9/1983 | Rajadhyaksha | 424/244 |
| 4,435,180 | 3/1984 | Leeper | 604/896 |
| 4,559,222 | 12/1985 | Enscore et al. | 424/28 |
| 4,568,343 | 2/1986 | Leeper et al. | 604/896 |
| 4,573,995 | 3/1986 | Chen et al. | 604/896 |
| 4,588,580 | 5/1986 | Gale et al. | 424/21 |
| 4,645,502 | 2/1987 | Gale et al. | 604/896 |

(List continued on next page.)

FOREIGN PATENT DOCUMENTS

| | | | |
|---|---|---|---|
| 0272918 | 6/1988 | European Pat. Off. | A61L 15/03 |
| 0272987 | 8/1988 | European Pat. Off. | A61K 9/70 |
| 0279986 | 8/1988 | European Pat. Off. | A61K 47/00 |
| 0425968 | 5/1991 | European Pat. Off. | A61K 9/70 |
| 0468875 | 1/1992 | European Pat. Off. | A61L 15/44 |
| 87/00042 | 1/1987 | WIPO | A61K 9/00 |
| 87/01291 | 3/1987 | WIPO | A61L 15/03 |
| 88/01496 | 3/1988 | WIPO | A61F 13/00 |
| 88/01497 | 3/1988 | WIPO | A61F 13/00 |
| 93/00058 | 1/1993 | WIPO | A61F 13/02 |
| 95/09006 | 4/1995 | WIPO | A61K 47/14 |

OTHER PUBLICATIONS

Shah, Hemanshu S., et al., Drug Development and Industrial Pharmacy, vol. 18 (13), pp. 1461–1476 (1992), "Enhancement Of In Vitro Skin Permeation Of Verapamil".

*Primary Examiner*—D. Gabrielle Brouillette
*Attorney, Agent, or Firm*—Michael J. Rafa; Steve F. Stone

[57] ABSTRACT

Compositions, devices, and methods for transdermal administration of an active agent are disclosed using a novel dual permeation enhancer mixture comprising lauryl acetate and a monoglyceride, preferably glycerol monolaurate. The dual permeation enhancer mixture comprising lauryl acetate is a potent permeation enhancer and provides stable systems which are more readily characterized.

19 Claims, 6 Drawing Sheets

U.S. PATENT DOCUMENTS

| | | | |
|---|---|---|---|
| 4,704,282 | 11/1987 | Campbell et al. | 424/449 |
| 4,746,515 | 5/1988 | Cheng et al. | 424/449 |
| 4,788,062 | 11/1988 | Gale et al. | 424/449 |
| 4,814,173 | 3/1989 | Song et al. | 424/444 |
| 4,816,258 | 3/1989 | Nedberge et al. | 424/448 |
| 4,820,720 | 4/1989 | Sanders et al. | 514/356 |
| 4,849,226 | 7/1989 | Gale | 424/448 |
| 4,863,738 | 9/1989 | Taskovich | 424/449 |
| 4,863,970 | 9/1989 | Patel et al. | 514/784 |
| 4,908,027 | 3/1990 | Enscore et al. | 604/890.1 |
| 4,943,435 | 7/1990 | Baker et al. | 424/448 |
| 4,954,487 | 9/1990 | Cooper et al. | 514/159 |
| 5,004,610 | 4/1991 | Osborne et al. | 424/448 |
| 5,026,556 | 6/1991 | Drust et al. | 424/449 |
| 5,122,382 | 6/1992 | Gale et al. | 424/449 |
| 5,149,538 | 9/1992 | Granger et al. | 424/449 |
| 5,162,410 | 11/1992 | Sweet | 524/266 |
| 5,186,939 | 2/1993 | Cleary et al. | 424/448 |
| 5,198,223 | 3/1993 | Gale et al. | 424/449 |
| 5,232,702 | 8/1993 | Pfister | 424/448 |
| 5,314,694 | 5/1994 | Gale | 424/448 |
| 5,320,850 | 6/1994 | Gale et al. | 424/449 |
| 5,352,456 | 10/1994 | Fallon et al. | 424/448 |
| 5,352,722 | 10/1994 | Sweet et al. | 524/266 |
| 5,376,377 | 12/1994 | Gale et al. | 424/448 |
| 5,378,730 | 1/1995 | Lee et al. | 514/535 |
| 5,601,839 | 2/1997 | Quan | 424/448 |

SKIN PERMEATION ENHANCER COMPOSITIONS COMPRISING GLYCEROL MONOLAURATE AND LAURYL ACETATE

RELATED APPLICATIONS

This application is a continuation-in-part of Ser. No. 08/481,549, now U.S. Pat. No. 5,785,991, filed Jun. 7, 1995, assigned to ALZA Corporation, for which the benefit of the earlier filing date is claimed.

TECHNICAL FIELD

This invention relates to the transdermal delivery of agents or other biologically active agents and more particularly to methods and compositions for enhancing the percutaneous absorption of agents or other agents when incorporated in transdermal agent delivery systems or devices. More particularly, this invention relates to the transdermal delivery of agents utilizing a novel dual permeation enhancer comprising glycerol monolaurate and lauryl acetate.

DESCRIPTION OF TERMS

As used herein, the term "transdermal" means percutaneous delivery of an agent through skin or mucosal tissue into the circulation by topical application.

As used herein, the term "therapeutically effective" amount or rate refers to the amount or rate of agent or active agent needed to achieve a desired therapeutic result.

As used herein, the phrase "predetermined area of skin" refers to a defined area of intact unbroken skin or mucosal tissue. That area is usually in the range of about 5 cm$^2$ to about 100 cm$^2$.

As used herein, the term "monoglyceride" refers to a monoglyceride of a fatty acid or a mixture of monoglycerides of fatty acids, or mixtures thereof with other materials in which the monoglyceride component comprises at least 50% by weight, and includes, for example, glycerol monolaurate, glycerol monooleate, and glycerol monolinoleate.

As used herein, "glycerol monolaurate" refers to glycerol monolaurate itself or a mixture of glycerides wherein glycerol monolaurate is present in the greatest amount.

As used herein, "glycerol monooleate" refers to glycerol monooleate itself or a mixture of glycerides wherein glycerol monooleate is present in the greatest amount.

As used herein, "glycerol monolinoleate" refers to glycerol monolinoleate itself or a mixture of glycerides wherein glycerol monolinoleate is present in the greatest amount.

As used herein, the phrase "water absorbing polymer" refers to a hydrophilic polymer being able to absorb water and includes, but is not limited to, polyvinyl pyrrolidones, polyvinyl alcohol, and polyaminoacrylates.

BACKGROUND ART

The transdermal route of parenteral delivery of drugs provides many advantages, and transdermal systems for delivering a wide variety of drugs or other beneficial agents are described in U.S. Pat. Nos. 3,598,122; 3,598,123; 3,731,683; 3,797,494; 4,286,592; 4,314,557; 4,379,454; 4,435,180; 4,559,222; 4,568,343; 4,573,999; 4,588,580; 4,645,502; 4,704,282; 4,816,258; 4,849,226; 4,908,027; 4,943,435; and 5,004,610, for example, all of which are incorporated herein by reference. In many cases, agents which would appear to be ideal candidates for transdermal delivery are found to have such low permeability through intact skin that they cannot be delivered in therapeutically effective amounts from reasonably sized devices.

In an effort to increase skin permeability so that agents can be delivered in therapeutically effective amounts at therapeutically effective rates, it has been proposed to pretreat the skin with various chemicals or to concurrently deliver the agent in the presence of a permeation enhancer. Various materials have been suggested for this, as described in. U.S. Pat. Nos. 3,472,931; 3,527,864; 3,896,238; 3,903,256; 3,952,099; 4,046,886; 4,130,643; 4,130,667; 4,299,826; 4,335,115; 4,343,798; 4,379,454; 4,405,616; 4,746,515; 4,788,062; 4,820,720; 4,863,738; 4,863,970; and 5,378,730; British Pat. No. 1,011,949; and Idson, "Percutaneous Absorption," J. Pharm. Sci. (1975) 64:901–924.

To be considered useful, a permeation enhancer should have the ability to enhance the permeability of the skin for at least one and preferably a significant number of agents. More importantly, it should be able to enhance the skin permeability such that the agent delivery rate from a reasonably sized system (preferably 5–50 cm$^2$) is at therapeutic levels. Additionally, the enhancer when applied to the skin surface, should be non-toxic, non-irritating on prolonged exposure and under occlusion, and non-sensitizing on repeated exposure. Preferably, it should be odorless and capable of delivering agents without producing burning or tingling sensations.

It is often difficult to predict which compounds will work as permeation enhancers and which permeation enhancers will work for particular agents. In systemic drug delivery applications, a compound that enhances the permeability of one agent or a family of agents may not necessarily enhance the permeability of another agent or family of agents. Therefore, the usefulness of a particular compound as a permeation enhancer must be analyzed carefully.

U.S. Pat. No. 4,954,487 and European Patent Application 0 043 738 disclose pharmaceutical compositions containing a penetrating vehicle consisting essentially of a $C_1$–$C_4$ diol compound and a cell envelope disordering compound. Lauryl acetate is disclosed as a suitable cell envelope disordering compound.

U.S. Pat. No. 5,026,556 discloses a composition for the transdermal delivery of buprenorphine comprising an amount of buprenorphine in a carrier comprising a polar solvent material selected from the group consisting of $C_3$–$C_4$ diols, $C_3$–$C_6$ triols, and mixtures thereof; and a polar lipid material selected from the group consisting of fatty alcohol esters, fatty acid esters, and mixtures thereof. Lauryl acetate is disclosed as a suitable polar lipid material.

U.S. Pat. No. 5,149,538 discloses the transdermal delivery of an opioid. Preferred permeation enhancers are saturated and unsaturated fatty alcohols, fatty alcohol esters, or fatty acids having 8–18 carbon atoms. All of the aforementioned patents are incorporated herein in their entirety by reference.

While it is known in the art to combine permeation enhancers, this invention utilizes a novel combination of dodecyl acetate (lauryl acetate) and glycerol monolaurate (GML), and the combined effect is a significant and surprising improvement over use of GML or lauryl acetate alone.

DISCLOSURE OF THE INVENTION

It has been found that GML, known to enhance agent permeation in vitro, does not exhibit a good in vitro/in vivo correlation. Results derived from in vivo testing using GML as a permeation enhancer have not been found to be as consistent as the results from in vitro tests. Cosolvents such as lauryl lactate, ethyl lactate, and myristyl lactate all have the potential to effectively enhance agent permeation when combined with GML. However, these combinations of cosolvents and GML perform inconsistently from one lot of formulations to another.

According to this invention, we believe that this inconsistent performance can be attributed to the fact that these cosolvents are not obtainable at a high degree of purity. The lauryl lactate used in the Examples that follow, for example, was obtained as two different mixtures: Ceraphyl 31 or a purer lauryl lactate (both from ISP Van Dyk, Bellevue, N.J.). Ceraphyl 31 is a mixture of 50.6% lauryl lactate, 19.1% myristyl lactate, 8.8% lauryl alcohol, 8.3% palmityl lactate, 3:7% stearyl lactate, and 3.5% myristyl alcohol. The purer lauryl lactate is available as a mixture of 82.8% lauryl lactate, 11% lauryl lactyllactate, and 4% 1-dodecanol.

In addition to the problem of inconsistent performance, the failure to obtain a cosolvent at a high degree of purity also makes it difficult to characterize the system in which the mixture is used. Therefore, cosolvents such as Ceraphyl 31 may not be usable in products subject to regulatory review.

According to this invention, lauryl acetate, a cosolvent obtainable at a high degree of purity, has been found to reduce or eliminate the problems of inconsistency and characterization.

Accordingly, the present invention provides a composition of matter for application to a body surface or membrane to deliver at least one agent, at a therapeutically effective rate, by permeation through the body surface or membrane, comprising at least one agent and a permeation-enhancing amount of lauryl acetate and a monoglyceride or mixture of monoglycerides of a fatty acid. The invention further provides a method for the transdermal coadministration of a agent at a therapeutically effective rate together with a skin permeation-enhancing amount of lauryl acetate and a monoglyceride or mixture of monoglycerides of a fatty acid. The monoglyceride is preferably glycerol monolaurate.

It is accordingly an aspect of this invention to provide a permeation enhancer composition for use in transdermal compositions, methods, and devices which provides for the transdermal coadministration of an agent at a therapeutically effective rate with improved in vivo efficacy.

It is another aspect of this invention to provide a permeation enhancer composition for use in transdermal compositions, methods, and devices comprising a monoglyceride and a cosolvent wherein the cosolvent is stable and obtainable at a high degree of purity, thus resulting in systems which are more readily characterized.

It is yet another aspect of this invention to provide a permeation enhancer composition for use in transdermal compositions, methods, and devices which provides consistent results from one lot of formulations to another.

These and other aspects and advantages of this invention will be readily apparent from the following description with reference to the accompanying figures.

MODES FOR CARRYING OUT THE INVENTION

Figure 1:
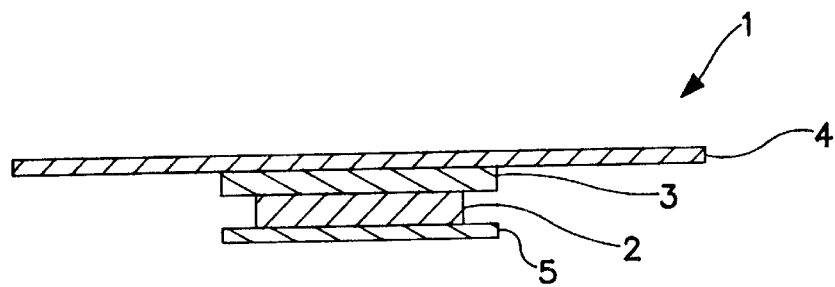
FIG. 1 is a cross-sectional view of one embodiment of a transdermal therapeutic agent delivery device which may be used in accordance with the present invention.

According to the invention, GML is combined with lauryl acetate as a cosolvent to provide an improved permeation enhancer mixture. Lauryl acetate, obtainable at 97–99% purity, is effective as a cosolvent for GML and effectively enhances the permeation of various agents through the skin. The combination of lauryl acetate and GML is a potent permeation enhancer mixture which is non-irritating to the skin, provides consistent results, and provides a system which is more readily characterized than other GML/cosolvent mixtures using cosolvents of lower purity.

In addition to its higher degree of purity, lauryl acetate also has greater stability than lauryl lactate and can solubilize a larger amount of GML, thus it may allow for a greater amount of GML to reach the skin. A preferred permeation enhancer composition of this invention comprises lauryl acetate of about 97–99% purity together with GML. It is further preferable that the lauryl acetate of at least 97% purity be used in combination with a monoglyceride containing at least 50% of the principal monoglyceride component and having a monoester content of at least 51%.

It has now been found that a combination of GML and lauryl acetate can be used to effectively enhance the permeability of agents through body surfaces and particularly through the skin. Specifically, it has been found that GML and lauryl acetate enhance the permeability of the skin such that therapeutically effective amounts of an agent can be delivered from reasonably sized devices at therapeutically effective rates.

The system of the invention is preferably a transdermal agent delivery device comprising a matrix adapted to be placed in agent- and permeation enhancer-transmitting relation with the skin or mucosa. The system must be of a size useful for the application of the agent and the enhancer to a human body.

The utility of a GML/lauryl acetate dual permeation enhancer has been demonstrated for a variety of different agents as seen in the Examples that follow. It is believed that this invention has utility in connection with the delivery of agents within the broad class normally delivered through body surfaces and membranes, including skin. In general, this includes therapeutic agents in all of the major areas, including, but not limited to, ACE inhibitors, adenohypophoseal hormones, adrenergic neuron blocking agents, adrenocortical steroids, inhibitors of the biosynthesis of adrenocortical steroids, alpha-adrenergic agonists, alpha-adrenergic antagonists, selective alpha-two-adrenergic agonists, analgesics, antipyretics and anti-inflammatory agents, androgens, local and general anesthetics, antiaddictive agents, antiandrogens, antiarrhythmic agents, antiasthmatic agents, anticholinergic agents, anticholinesterase agents, anticoagulants, antidiabetic agents, antidiarrheal agents, antidiuretic, antiemetic and prokinetic agents, antiepileptic agents, antiestrogens, antifungal agents, antihypertensive agents, antimicrobial agents, antimigraine agents, antimuscarinic agents, antineoplastic agents, antiparasitic agents, antiparkinson's agents, antiplatelet agents, antiprogestins, antithyroid agents, antitussives, antiviral agents, atypical antidepressants, azaspirodecanediones, barbituates, benzodiazepines, benzothiadiazides, beta-adrenergic agonists, betaadrenergic antagonists, selective beta-one-adrenergic antagonists, selective beta-two-adrenergic agonists, bile salts, agents affecting volume and composition of body fluids, butyrophenones, agents affecting calcification, calcium channel blockers, cardiovascular drugs, catecholamines and sympathomimetic drugs, cholinergic agonists, cholinesterase reactivators, dermatological agents, diphenylbutylpiperidines, diuretics, ergot alkaloids, estrogens, ganglionic blocking agents, ganglionic stimulating agents, hydantoins, agents for control of gastric acidity and treatment of peptic ulcers, hematopoietic agents, histamines, histamine antagonists, 5-hydroxytryptamine antagonists, drugs for the treatment of hyperlipoproteinemia, hypnotics and sedatives, immunosupressive agents, laxatives, methylxanthines, monoamine oxidase inhibitors, neuromuscular blocking agents, organic nitrates, opiod analgesics and antagonists, pancreatic enzymes, phenothiazines, progestins, prostaglandins, agents for the treatment of psychiatric disorders, retinoids, sodium channel blockers, agents for spasticity and acute muscle spasms, succinimides, thioxanthines, thrombolytic agents, thyroid agents, tricyclic antidepressants, inhibitors of tubular transport of organic compounds, drugs affecting uterine motility, vasodilators, vitamins and the like.

Representative agents include, by way of example and not for purposes of limitation, bepridil, diltiazem, felodipine, isradipine, nicardipine, nifedipine, nimodipine, nitredipine, verapamil, dobutamine, isoproterenol, carterolol, labetalol, levobunolol, nadolol, penbutolol, pindolol, propranolol, sotalol, timolol, acebutolol, atenolol, betaxolol, esmolol, metoprolol, albuterol, bitolterol, isoetharine, metaproterenol, pirbuterol, ritodrine, terbutaline, alclometasone, aldosterone, amcinonide, beclomethasone dipropionate, betamethasone, clobetasol, clocortolone, cortisol, cortisone, corticosterone, desonide, desoximetasone, 11-desoxycorticosterone, 11-desoxycortisol, dexamethasone, diflorasone, fludrocortisone, flunisolide, fluocinolone, fluocinonide, fluorometholone, flurandrenolide, halcinonide, hydrocortisone, medrysone, 6α-methylprednisolone, mometasone, paramethasone, prednisolone, prednisone, tetrahydrocortisol, triamcinolone, benoxinate, benzocaine, bupivacaine, chloroprocaine, cocaine, dibucaine, dyclonine, etidocaine, lidocaine, mepivacaine, pramoxine, prilocaine, procaine, proparacaine, tetracaine, alfentanil, choroform, clonidine, cyclopropane, desflurane, diethyl ether, droperidol, enflurane, etomidate, fentanyl, halothane, isoflurane, ketamine hydrochloride, meperidine, methohexital, methoxyflurane, morphine, propofol, sevoflurane, sufentanil, thiamylal, thiopental, acetaminophen, allopurinol, apazone, aspirin, auranofin, aurothioglucose, colchicine, diclofenac, diflunisal, etodolac, fenoprofen, flurbiprofen, gold sodium thiomalate, ibuprofen, indomethacin, ketoprofen, meclofenamate, mefenamic acid, meselamine, methyl salicylate, nabumetone, naproxen, oxyphenbutazone, phenacetin, phenylbutazone, piroxicam, salicylamide, salicylate, salicylic acid, salsalate, sulfasalazine, sulindac, tolmetin, acetophenazine, chlorpromazine, fluphenazine, mesoridazine, perphenazine, thioridazine, trifluorperazine, triflupromazine, disopyramide, encainide, flecainide, indecainide, mexiletine, moricizine, phenytoin, procainamide, propafenone, quinidine, tocainide, cisapride, domperidone, dronabinol, haloperidol, metoclopramide, nabilone, prochlorperazine, promethazine, thiethylperazine, trimethobenzamide, buprenorphine, butorphanol, codeine, dezocine, diphenoxylate, drocode, hydrocodone, hydromorphone, levallorphan, levorphanol, loperamide, meptazinol, methadone, nalbuphine, nalmefene, nalorphine, naloxone, naltrexone, oxybutynin, oxycodone, oxymorphone, pentazocine, propoxyphene, isosorbide dinitrate, nitroglycerin, theophylline, phenylephrine, ephidrine, pilocarpine, furosemide, tetracycline, chlorpheniramine, ketorolac, bromocriptine, guanabenz, prazosin, doxazosin, and flufenamic acid.

Other representative agents include benzodiazepines, such as alprazolam, brotizolam, chlordiazepoxide, clobazam, clonazepam, clorazepate, demoxepam, diazepam, flumazenil, flurazepam, halazepam, lorazepam, midazolam, nitrazepam, nordazepam, oxazepam, prazepam, quazepam, temazepam, triazolam, and the like; an antimuscarinic agent such as anisotropine, atropine, clidinium, cyclopentolate, dicyclomine, flavoxate, glycopyrrolate, hexocyclium, homatropine, ipratropium, isopropamide, mepenzolate, methantheline, oxyphencyclimine, pirenzepine, propantheline, scopolamine, telenzepine, tridihexethyl, tropicamide, and the like; an estrogen such as chlorotrianisene, siethylstilbestrol, methyl estradiol, estrone, estrone sodium sulfate, estropipate, mestranol, quinestrol, sodium equilin sulfate, 17β-estradiol (or estradiol), semi-synthetic estrogen derivatives such as the esters of natural estrogen, such as estradiol-17β-enanthate, estradiol-17β-valerate, estradiol-3-benzoate, estradiol-17β-undecenoate, estradiol 16,17-hemisuccinate or estradiol-17β-cypionate, and the 17-alkylated estrogens, such as ethinyl estradiol, ethinyl estradiol-3-isopropylsulphonate, and the like; an androgen such as danazol, fluoxymesterone, methandrostenolone, methyltestosterone, nandrolone, nandrolone decanoate, nandrolone phenpropionate, oxandrolone, oxymetholone, stanozolol, testolactone, testosterone, testosterone cypionate, testosterone enanthate, testosterone propionate, and the like; or a progestin such as ethynodiol diacetate, gestodene, hydroxyprogesterone caproate, levonorgestrel, medroxyprogesterone acetate, megestrol acetate, norethindrone, norethindrone acetate, norethynodrel, norgestrel, progesterone, and the like.

Lauryl acetate has been demonstrated herein as a suitable cosolvent for GML. Lauryl acetate may also be used as a cosolvent together with other monoglycerides. Typically, monoglycerides have been available as a mixture of monoglycerides of fatty acids with one monoglyceride being the principal component, from which component the mixture derives its name. For example, one commercial monoglyceride is Emerest 2421 glycerol monooleate (Emery Division, Quantum Chemical Corp.), which is a mixture of glycerol oleates with a glycerol monooleate content of 58% by weight and a total monoesters content of 58% by weight.

Other examples of commercial monoglycerides are Myverol 1899K glycerol monooleate (Eastman Chemical Products) which has a glycerol monooleate content of 61% and a total monoesters content of 93%, and Myverol 1892K glycerol monolinoleate which has a glycerol monolinoleate content of 68% and a minimum total monoesters content of 90%. The monoesters are chosen from those with from 10 to 20 carbon atoms. The fatty acids may be saturated or unsaturated and include, for example, lauric acid, myristic acid, stearic acid, oleic acid, linoleic acid and palmitic acid. Monoglyceride permeation enhancers include glycerol monooleate, glycerol monolaurate and glycerol monolinoleate, for example.

Transdermal agent delivery systems are typically maintained in contact with the skin using an "in-line" contact adhesive, ie, a layer of adhesive positioned between the agent reservoir of the delivery system and the skin. Glycerol monooleate having a total monoesters content of less than about 65% interacts adversely with known adhesive materials to such an extent that the adhesive cannot function to maintain a delivery device on the skin. Therefore, when an in-line adhesive is present as a part of the device of the invention so that a permeation enhancer must pass through the adhesive, and when glycerol monooleate is utilized as the second permeation enhancer, the glycerol monooleate must have a total monoesters content of at least 65%.

Administration of the agent according to the invention comprises administering the agent at a therapeutically effective rate to an area of a body surface (eg, skin) or membrane and simultaneously administering GML and lauryl acetate to the area of the body surface or membrane at rates which are sufficient to substantially increase the permeability of the area to the agent formulation.

According to the invention, the GML and lauryl acetate mixture and the agent to be delivered are placed in agent- and permeation enhancer-transmitting relationship to the appropriate body surface, preferably in a carrier therefor, and maintained in place for the desired period of time. The agent and permeation enhancer mixture are typically dispersed within a physiologically compatible matrix or carrier which may be applied directly to the body surface or skin as an ointment, gel, cream, suppository or sublingual or buccal tablet, for example, but are more preferably administered from a transdermal therapeutic delivery device as more fully described below. When used in the form of a liquid, ointment, cream, or gel applied directly to the skin, it is preferable, although not required, to occlude the site of administration. Such compositions can also contain other permeation enhancers, stabilizers, dyes, diluents, pigments, vehicles, inert fillers, excipients, gelling agents, vasoconstrictors, and other components of typical compositions as are known to the art.

The GML/lauryl acetate dual permeation enhancer of this invention has a permeation-enhancing effect on the transport of agents through body surface tissues generally, in addition to the skin. However, because skin is one of the most effective barriers to the permeation of agents into the body, the effect of GML and lauryl acetate on skin permeation makes it extremely useful in transdermal delivery. The following description of embodiments of the invention is therefore directed primarily to improving systemic delivery of these agents by permeation through the skin.

One embodiment of a transdermal delivery device of the present invention is illustrated in FIG. 1. In FIG. 1, device 1 is comprised of a agentand permeation enhancer-containing reservoir ("agent reservoir") 2 which is preferably in the form of a matrix containing the agent and the enhancer dispersed therein. An impermeable backing layer 3 is provided adjacent one surface of agent reservoir 2. Adhesive overlay 4 maintains the device 1 on the skin and may be fabricated together with, or provided separately from, the remaining elements of the device. With certain formulations, the adhesive overlay 4 may be preferable to an in-line contact adhesive, such as adhesive layer 28 as shown in FIG. 3. Impermeable backing layer 3 is preferably slightly larger than agent reservoir 2, and in this manner prevents the materials in agent reservoir 2 from adversely interacting with the adhesive in overlay 4. A strippable or removable liner 5 is also provided with device 1 and is removed just prior to application of device 1 to the skin.

FIG. 2 illustrates another embodiment of the invention, device 10, shown in placement on the skin 17. In this embodiment, the transdermal agent delivery device 10 comprises multi-laminate agent formulation/enhancer reservoir 11 having at least two zones 12 and 14. Zone 12 consists of an agent reservoir substantially as described with respect to FIG. 1. Zone 14 comprises a permeation enhancer reservoir which is preferably made from substantially the same matrix as is used in zone 12. Zone 14 comprises GML and lauryl acetate dispersed throughout and is substantially free of any undissolved agent. A rate-controlling membrane 13 for controlling the release rate of the GML/lauryl acetate mixture from zone 14 to zone 12 is placed between the two zones. A rate-controlling membrane (not shown) for controlling the release rate of the enhancer from zone 12 to the skin may also optionally be utilized and would be present between the skin 17 and zone 12.

The rate-controlling membrane 13 may be fabricated from permeable, semipermeable or microporous materials which are known in the art to control the rate of agents into and out of delivery devices and having a permeability to the permeation enhancer lower than the matrix material of zone 12. Suitable materials include, but are not limited to, polyethylene, polyvinyl acetate and ethylene vinyl acetate copolymers.

An advantage of the device described in FIG. 2 is that the agent-loaded zone 12 is concentrated at the skin surface rather than throughout the entire mass of a combined agent and enhancer reservoir such as reservoir 2 in FIG. 1. This reduces the amount of agent in the device while maintaining an adequate supply of permeation enhancer.

Superimposed over the agent formulation/enhancer reservoir 11/12 of device 10 is an impermeable backing 15 and an adhesive overlay 16 as described above with respect to FIG. 1. In addition, a strippable liner (not shown) would preferably be provided on the device prior to use as described with respect to FIG. 1 and removed prior to application of the device 10 to the skin 17.

In the embodiments of FIGS. 1 and 2, the carrier or matrix material has sufficient viscosity to maintain its shape without oozing or flowing. If, however, the matrix or carrier is a low viscosity flowable material, the composition can be fully enclosed in a permeable or microporous skin-contacting membrane, as known to the art from U.S. Pat. No. 4,379,454 (noted above), for example.

Another embodiment is illustrated in FIG. 3. Device 20 comprises an agent reservoir 22 containing both the agent and the GML/lauryl acetate permeation enhancer. Reservoir 22 is preferably in the form of a matrix containing the agent and the enhancer dispersed therein. Reservoir 22 is sandwiched between a backing layer 24, which is preferably impermeable to both the agent and the permeation enhancer mixture, and an in-line contact adhesive layer 28. In FIG. 3, the agent reservoir 22 is formed of a material, such as a rubbery polymer, that is sufficiently viscous to maintain its shape. The device 20 adheres to the surface of the skin 17 by means of the contact adhesive layer 28. The adhesive for layer 28 should be chosen so that it is compatible and does not interact with any of the agent or, in particular, the GML/lauryl acetate permeation enhancer. The adhesive layer 28 may optionally contain enhancer and/or agent. A strippable liner (not shown) is normally provided along the exposed surface of adhesive layer 28 and is removed prior to application of device 20 to the skin 17. In an alternative embodiment, a rate-controlling membrane (not shown) is present and the agent reservoir 22 is sandwiched between backing layer 24 and the rate-controlling membrane, with adhesive layer 28 present on the skin-side of the rate-controlling membrane.

Figure 2:
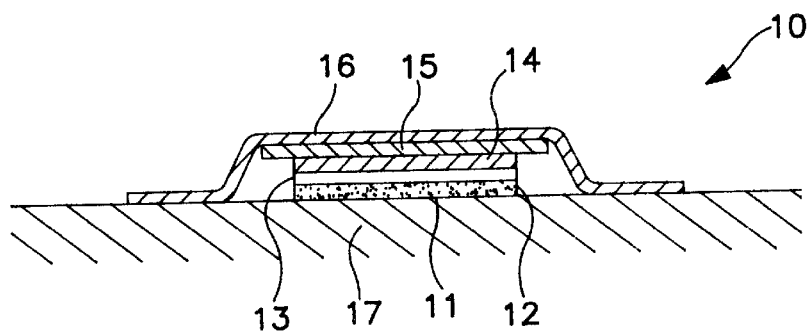
FIG. 2 is a cross-sectional view of another embodiment of a transdermal therapeutic agent delivery device which may be used in accordance with the present invention.
Figure 3:
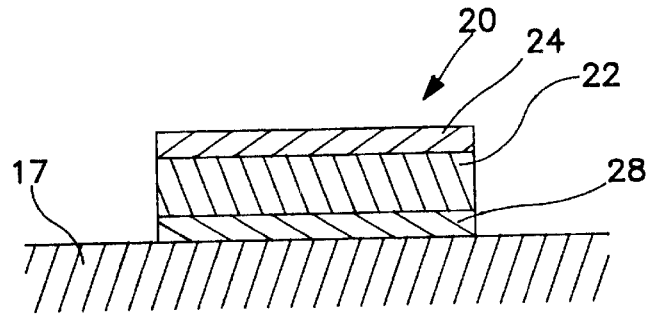
FIG. 3 is a cross-sectional view of yet another embodiment of a transdermal therapeutic agent delivery device which may be used in accordance with this invention.

Various materials suited for the fabrication of the various layers of the transdermal devices of FIGS. 1–3 are known in the art or are disclosed in the aforementioned transdermal device patents previously incorporated herein by reference.

The matrix making up the agent/permeation enhancer reservoir of FIGS. 1–3 can be a gel or a polymer. Suitable materials are compatible with the agent, GML or other monoglyceride, lauryl acetate, and any other components in the system. Suitable matrix materials include, without limitation, natural and synthetic rubbers or other polymeric material, thickened mineral oil, or petroleum jelly, for example. The matrix is preferably polymeric and is more preferably an anhydrous polymer. A preferred embodiment according to this invention is fabricated from an ethylene vinyl acetate (EVA) copolymer, of the type described in U.S. Pat. No. 4,144,317, and is preferably selected from those EVAs having a vinyl acetate (VA) content in the range of about 9 to 60%, preferably about 28 to 60% VA. Particularly good results may be obtained using EVA of 40% vinyl acetate content.

In addition to an agent and GML/lauryl acetate, which are essential to he invention, the matrix, if needed, may also contain stabilizers, dyes, pigments, inert fillers, tackifiers, excipients and other conventional components of transdermal delivery devices as are known in the art.

Figure 4:
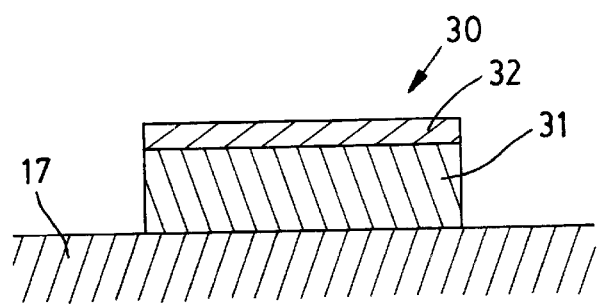
FIG. 4 is a cross sectional view of another embodiment of a transdermal therapeutic agent delivery device which may be used in accordance with this invention.

FIG. 4 depicts another preferred embodiment of the present invention. Device 30 includes a matrix 31 having agent and the GML/lauryl acetate permeation enhancer mixture dispersed therein and can additionally include a backing layer 32 to contain the agent and prevent its loss. Matrix 31 also preferably, but not necessarily, contains a water absorbing polymer to improve the long term wearability of the matrix system. A release liner (not shown in FIG. 4) may also be included and is removed prior to placing the device onto the skin 17.

The matrix material 31 comprises a hydrophobic pressure sensitive adhesive and preferably comprises a polysiloxane adhesive. The water absorbing polymers useful with the present invention are known in the art and include, for example, polyvinyl pyrrolidone, cross-linked polyvinyl pyrrolidone, polyaminoacrylates, and polyvinyl alcohol. Polyvinyl pyrrolidone is preferred.

The backing layer 32 is an elastomeric sheet or film that is substantially impermeable to the selected agent and permeation enhancers and has a thickness of about 1 micrometer to 100 micrometers. Suitable backing materials are known in the art and include, for example, low or medium density polyethylene, polyproylene, polyesters, and silicone elastomers.

According to a preferred embodiment of the matrix system depicted in FIG. 4, device 30 is prepared by extruding and calendering the adhesive composition between two differential release substrates. One of these release substrates is subsequently removed and the system is laminated to a backing layer.

Hot melt processing of the adhesive composition is accomplished by adding to the polysiloxane adhesive, which is dissolved in a carrier solvent, excipients which can plasticize the polysiloxane adhesive. This enables the excipients to be finely mixed into the solution. The carrier solvent is subsequently evaporated off, resulting in a pressure sensitive adhesive that is already plasticized by the excipients. The adhesive can then be mixed with additional excipients, such as active agents and water absorbing polymers, using blending equipment known in the art and subsequently hot melt processed in manufacturing.

According to this preferred embodiment, the plasticizing excipients are permeation enhancers which are capable of plasticizing the polysiloxane adhesive to a much lower complex viscosity and significantly lower the viscosity at time scales corresponding to process shear rates, typically of about 100 rad/sec. Suitable complex dynamic viscosities for the extrudable adhesive composition range from $10^3$–$10^7$ Poise, depending upon the processing temperature and shear rate. Glycerol monolaurate and lauryl acetate are the preferred plasticizing excipients.

The amounts of the agent that are present in the therapeutic devices depicted in FIGS. 1–4 required to achieve a therapeutic effect depend on many factors, such as the minimum necessary dosage of the particular agent; the permeability of the matrix, of the adhesive layer and of the rate-controlling membrane, if present; and the period of time for which the device will be fixed to the skin. There is, in fact, no upper limit to the maximum amounts of agent present in the device. The minimum amount of each agent is determined by the requirement that sufficient quantities of agent must be present in the device to maintain the desired rate of release over the given period of application.

The agent is generally dispersed through the matrix at a concentration in excess of saturation, i.e. at unit activity. The amount of excess is determined by the intended useful life of the system. However, the agent may be present at initial levels below saturation without departing from this invention. Generally, the agent may be present at initially subsaturated levels when: 1) the skin flux of the agent is sufficiently low such that the reservoir agent depletion is slow and small; 2) non-constant delivery of the agent is desired or acceptable; and/or 3) saturation of the reservoir is achieved in use due to migration of water into the reservoir from the skin, where water is abundantly available.

The GML and lauryl acetate mixture is dispersed throughout the matrix, preferably at a concentration sufficient to provide permeation-enhancing concentrations of enhancer in the reservoir throughout the anticipated administration period.

In the present invention, the agent is delivered through the skin or other body surface at a therapeutically effective rate (that is, a rate that provides an effective therapeutic result) and the GML/lauryl acetate dual permeation enhancer is delivered at a permeation-enhancing rate (that is, a rate that provides increased permeability of the application site to the agent) for a predetermined time period.

A preferred embodiment of the present invention is a device such as that illustrated in FIG. 3 (either with or without a rate-controlling membrane) wherein reservoir 22 comprises, by weight, 30–80% polymer (preferably EVA having a vinyl acetate content of 40%), 0.1–30% agent, 1–40% GML, and 1–40% lauryl acetate. The in-line adhesive layer 28 comprises an adhesive which is compatible with the permeation enhancer. A particularly preferred embodiment is a device as described above wherein the permeation enhancer mixture of glycerol monolaurate and lauryl acetate comprises 20% GML and 12% lauryl acetate.

Another preferred embodiment of the present invention is a matrix system such as that illustrated in FIG. 4 wherein the matrix comprises, by weight, 40–90% polymer (preferably a polysiloxane adhesive), 0.1–25% polyvinyl pyrrolidone, 0.1–30% agent, 1–30% GML, and 1–30% lauryl acetate.

The devices of this invention can be designed to effectively deliver a agent for an extended time period of up to 7 days or longer. Seven days is generally the maximum time limit for application of a single device because the skin site is adversely affected by a period of occlusion greater than 7 days. Where it is desired to have agent delivery for greater than 7 days (such as, for example, when a hormone is being applied for a contraceptive effect), when one device has been in place on the skin for its effective time period, it is replaced with a fresh device, preferably on a different skin site.

The transdermal therapeutic devices of the present invention are prepared in a manner known in the art, such as by those procedures, for example, described in the transdermal device patents listed previously herein. The following examples are offered to illustrate the practice of the present invention and are not intended to limit the invention in any manner.

EXAMPLE 1

The effect of various permeation enhancer mixtures on the transdermal flux of alprazolam was studied. The agent/permeation enhancer reservoirs were prepared by mixing ethylene vinyl acetate having a vinyl acetate content of 40 percent ("EVA 40", USI Chemicals, Illinois) in an internal mixer (Brabender type) until the EVA 40 pellets fused. Alprazolam, GML, glycerol monooleate (GMO), lauryl acetate (Penta International Corp., Livingston, N.J.), lauryl lactate, and myristyl lactate were then added as shown in Table 1. The mixture was blended, cooled, and calendered to a 5 mil thick film.

The film was then laminated to a Medpar 0 (3M, St. Paul, Minn.) backing on one side and an acrylate contact adhesive (3M Acrylic MSP 041991 P) on the opposite side. The laminate was then cut into 2.54 cm$^2$ circles using a steel punch.

TABLE 1

Agent/Permeation Enhancer Reservoir Composition (weight percent)

| FORMULATION | WEIGHT PERCENT |
|---|---|
| Alprazolam/GML/lauryl acetate/EVA 40 | 15/20/12/53 |
| Alprazolam/GML/lauryl lactate/EVA 40 | 15/20/12/53 |
| Alprazolam/GML/lauryl lactate/EVA 40 | 15/13/27/45 |
| Alprazolam/GMO/EVA 40 | 15/30/55 |
| Alprazolam/GMO/lauryl lactate/EVA 40 | 15/20/12/53 |
| Alprazolam/GMO/myristyl lactate/EVA 40 | 15/20/12/53 |

Circular pieces of human epidermis were mounted on the receptor compartment of horizontal permeation cells with the stratum corneum facing the donor compartment of the cell. The release liner of the laminate was removed and the systems were centered over the stratum corneum side of the epidermis. The donor compartment was then clamped with the receptor compartment. A known volume of receptor solution (20 ml, 0.01M potassium phopsphate pH 6+2% isopropyl alcohol) was equilibrated at 35° C. and placed in the receptor compartment. Air bubbles were removed from the receptor compartment, the cell was capped and placed in a water bath shaker at 35° C.

Figure 5:
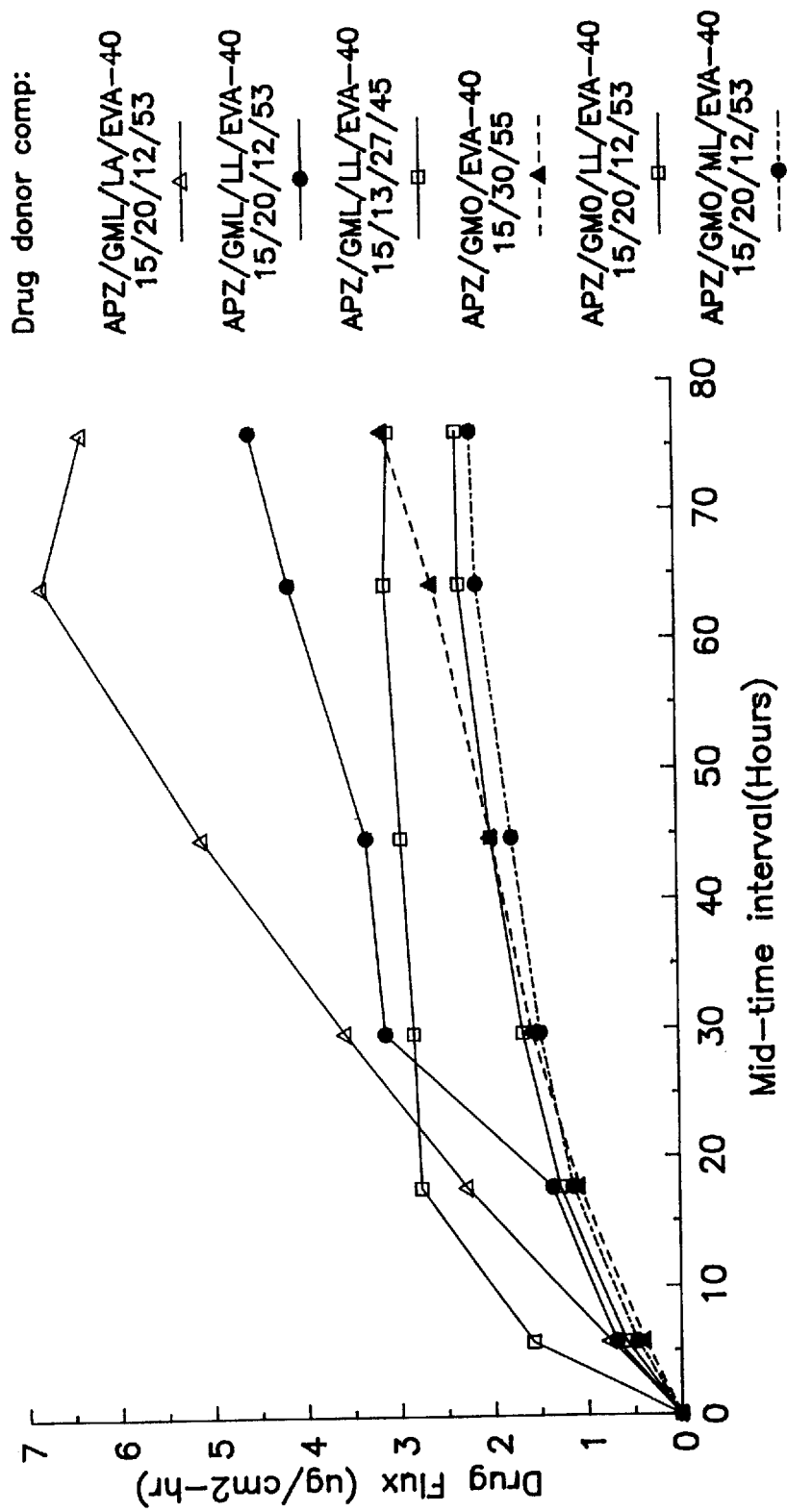
FIG. 5 is a graph of the flux of alprazolam through human epidermis at 35° C. from systems using various enhancers.

At given time intervals, the entire receptor solution was removed from the cells and replaced with an equal volume of fresh receptor solutions previously equilibrated at 35° C. The receptor solutions are stored in capped vials at 4° C. until assayed for alprazolam content by high performance liquid chromatography (HPLC). From the agent concentration and the volume of the receptor solutions, the area of permeation and the time interval, the flux of the agent through the epidermis was calculated as follows: (agent concentration×volume of receptor)/(area×time)=flux ($\mu$g/cm$^2$•hr). The transdermal fluxes of the various systems is shown in FIG. 5. As demonstrated in FIG. 5, the system comprising the GML/lauryl acetate permeation enhancer mixture achieved the greatest flux of alprazolam through skin.

EXAMPLE 2

The effect of GML and various cosolvents on the transdermal flux of oxybutynin was determined. The agent/permeation enhancer reservoirs, having the compositions shown in Table 2, were prepared by the procedure described in Example 1.

TABLE 2

Agent/Permeation Enhancer Reservoir Composition (weight percent)

| AGENT RESERVOIR | WEIGHT PERCENT |
|---|---|
| oxybutynin base/GML/EVA | 25/20/55 |
| oxybutynin base/GML/ceraphyl 31/EVA | 25/20/12/43 |
| oxybutynin base/GML/lauryl lactate/EVA | 25/20/12/43 |
| oxybutynin base/GML/methyl laurate/EVA | 25/20/12/43 |
| oxybutynin base/GML/lauryl acetate/EVA | 25/20/12/43 |

The agent reservoirs were then laminated to a water vapor permeable Sontara® spun laced polyester backing (code 80632B, DuPont, Wilmington Del.) on one side and a 1 mil thick Celgard® (Hoecsht Celanese, Charlotte, N.C.) film tie layer (microporous polypropylene) on the other. The laminate was then cut into 1.98 cm$^2$ circles using a steel punch. The punched systems were then weighed and placed in a 35° C. oven to equilibrate.

The in vitro transdermal oxybutynin permeation rates through human epidermis from the systems described above were determined. The systems tested were masked so that none of the device, except for the skin contacting surface, would be exposed to the receptor solution. For each system tested, the release liner was removed and the oxybutynin-releasing surface was centered and placed against the stratum corneum side of a disc of human epidermis which had been blotted dry just prior to use. The excess epidermis was wrapped around the device.

The assembly was then attached to the flat side of a Teflon® holder of a release rate rod using wire and nylon mesh. The rod with the system attached was placed into a 50 cc test tube filled with a known volume of receptor solution (0.05M phosphate solution, pH 6.0). Constant vertical stirring was accomplished by attaching the rod to a crossrod connected to an agitator that reciprocates the rod and system vertically in the test tube. The receptor solution was maintained at 35° C.

At given time intervals, the entire receptor solution was removed from the test tube and replaced with an equal volume of fresh receptor solution previously equilibrated at 35° C. The receptor solutions were stored in capped vials and refrigerated until assayed for oxybutynin content by HPLC.

Figure 6:
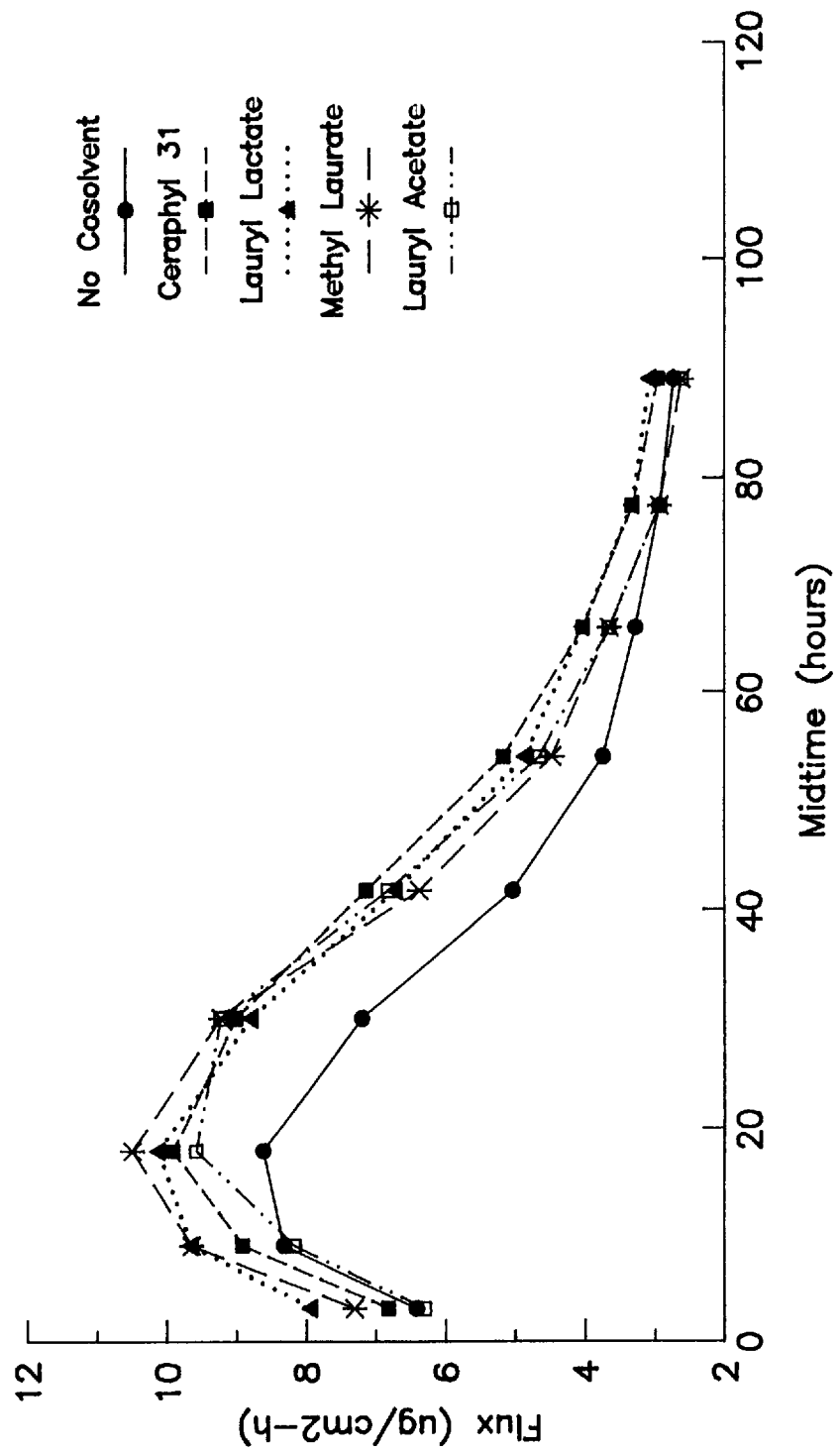
FIG. 6 is a graph of the flux of oxybutynin through human epidermis using various cosolvents for GML.

The transdermal flux of oxybutynin through human epidermis from these systems is shown in FIG. 6. As demonstrated in FIG. 6, the resultant skin flux of the GML/lauryl acetate formulation was greater than that of GML alone.

EXAMPLE 3

Systems comprising permeation enhancer mixtures of GML/lauryl acetate were compared to systems comprising mixtures of GML/lauryl lactate to observe the effect on the transdermal flux of alprazolam. Agent/permeation enhancer reservoirs, having the compositions shown in Table 3, were prepared by the procedures described in Example 1.

Figure 7:
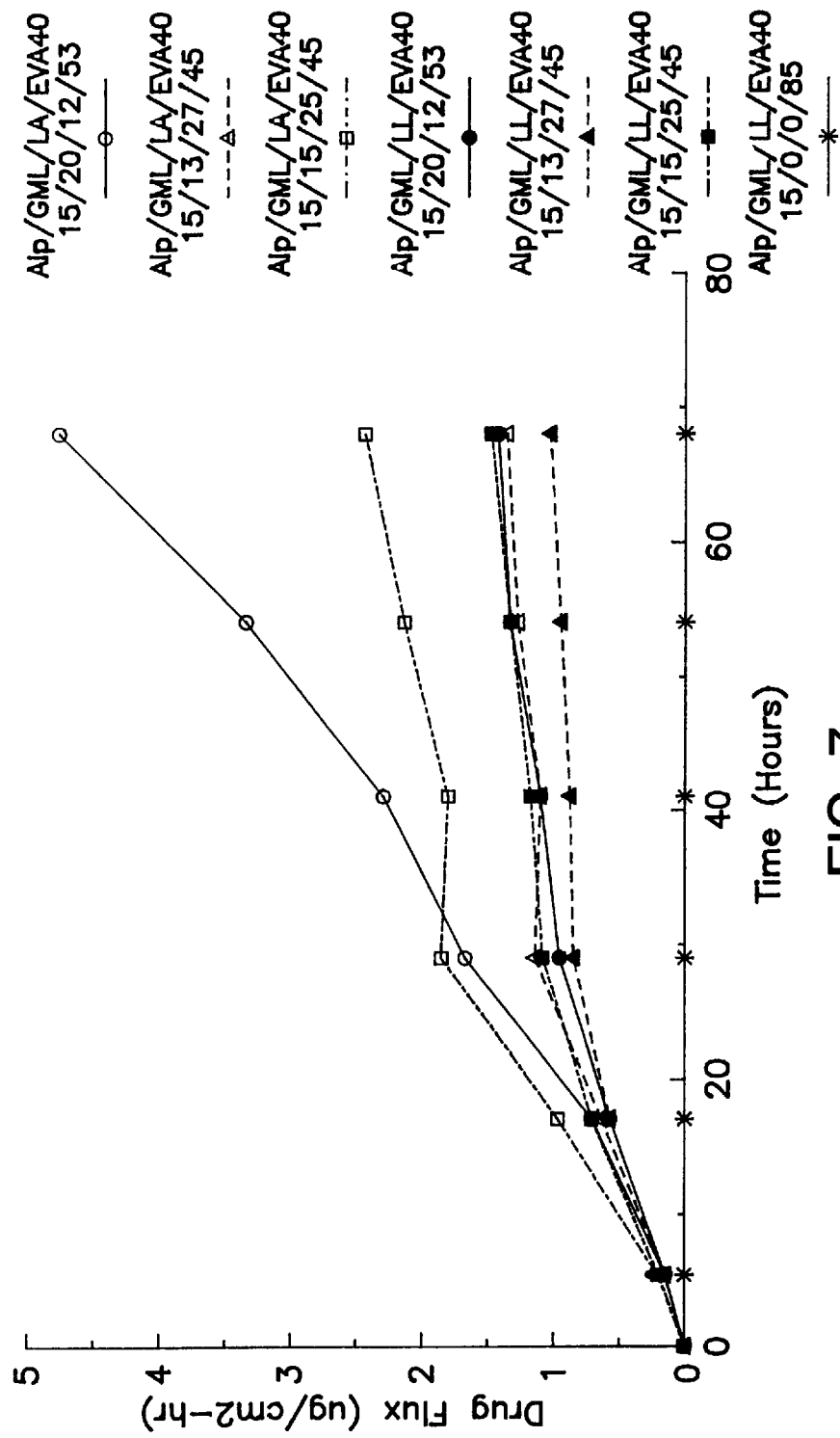
FIG. 7 is a graph of the flux of alprazolam through human epidermis at 35° C. from systems using various concentrations of GML with lauryl acetate or lauryl lactate.

These reservoir formulations were then used in transdermal flux studies using the same apparatus and procedures described in Example 1. The effect of the concentration of GML, lauryl acetate, and lauryl lactate on the flux of alprazolam through human epidermis from EVA 40 monoliths at 35° C. is shown in FIG. 7. As demonstrated in FIG. 7, the GML/lauryl acetate mixture provided a superior flux of alprazolam through skin of up to three times that of a GML/lauryl lactate mixture. The 15/25 mixture of GML/lauryl acetate reached steady state flux the quickest.

TABLE 3

Agent/Permeation Enhancer Reservoir Composition (weight percent)

| FORMULATION | WEIGHT PERCENT |
| --- | --- |
| Alprazolam/GML/lauryl acetate/EVA 40 | 15/20/12/53 |
| Alprazolam/GML/lauryl acetate/EVA 40 | 15/13/27/45 |
| Alprazolam/GML/lauryl acetate/EVA 40 | 15/15/25/45 |
| Alprazolam/GML/lauryl lactate/EVA 40 | 15/20/12/53 |
| Alprazolam/GML/lauryl lactate/EVA 40 | 15/13/27/45 |
| Alprazolam/GML/lauryl lactate/EVA 40 | 15/15/25/45 |
| Alprazolam/EVA 40 | 15/85 |

EXAMPLE 4

Agent/permeation enhancer reservoirs were prepared using the procedure of Example 3, substituting testosterone for alprazolam. The composition of the agent reservoirs is shown in Table 4.

TABLE 4

Agent/Permeation Enhancer Reservoir Composition (weight percent)

| FORMULATION | WEIGHT PERCENT |
| --- | --- |
| Testosterone/GML/lauryl acetate/EVA 40 | 15/20/12/53 |
| Testosterone/GML/lauryl acetate/EVA 40 | 15/13/27/45 |
| Testosterone/GML/lauryl acetate/EVA 40 | 15/15/25/45 |
| Testosterone/GML/lauryl lactate/EVA 40 | 15/20/12/53 |
| Testosterone/GML/lauryl lactate/EVA 40 | 15/13/27/45 |
| Testosterone/GML/lauryl lactate/EVA 40 | 15/15/25/45 |
| Testosterone/EVA 40 | 15/85 |

Figure 8:
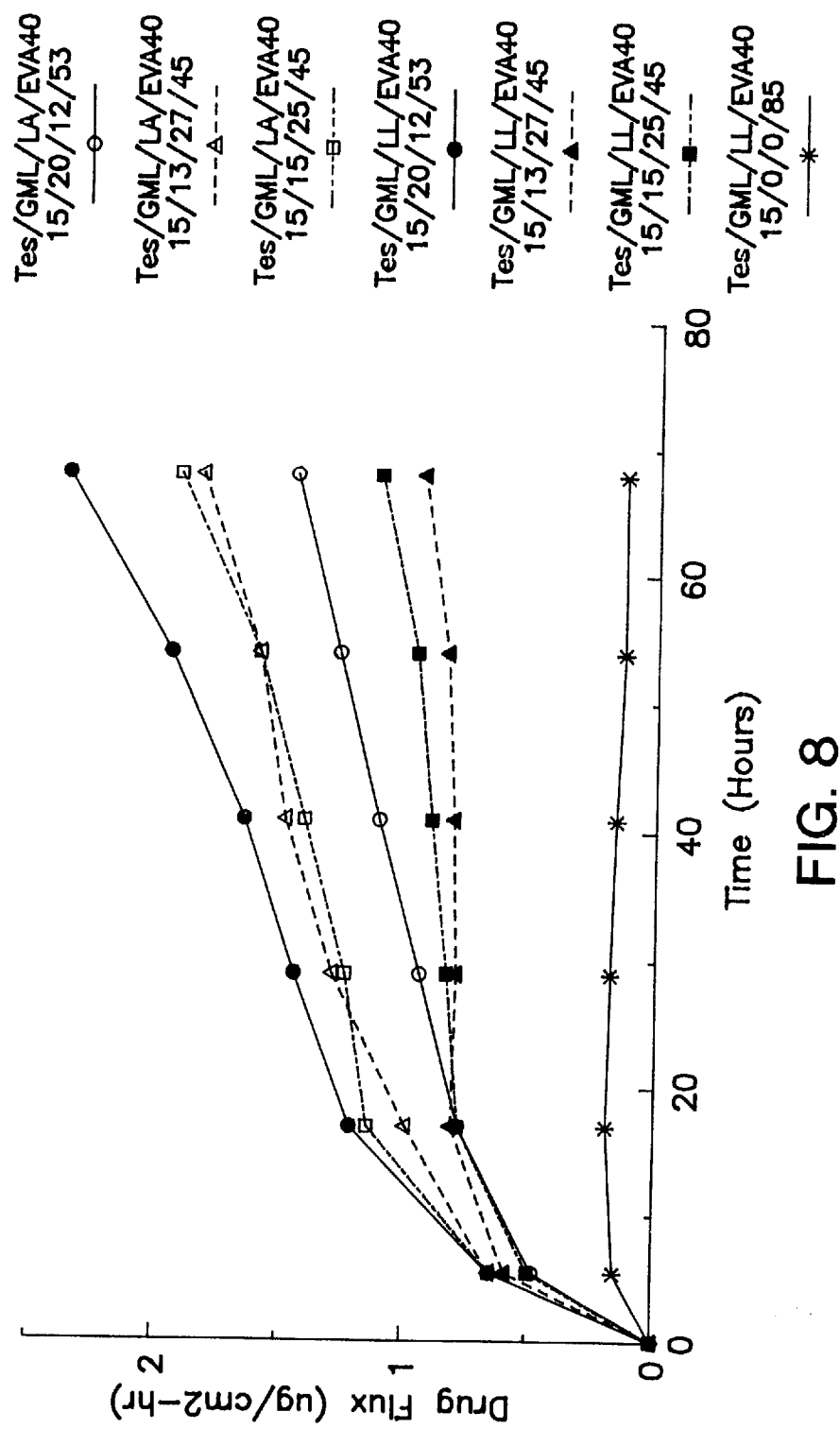
FIG. 8 is a graph of the flux of testosterone through human epidermis at 35° C. from systems using various concentrations of GML with lauryl acetate or lauryl lactate.

The skin flux experiment described in Example 1 was repeated for these systems, substituting 0.1% phenol as the receptor solution. The effect of the concentration of GML, lauryl acetate, and lauryl lactate on the flux of testosterone through human epidermis from EVA 40 monoliths at 35° C. is shown in FIG. 8.

EXAMPLE 5

A matrix type system according to FIG. 4 was prepared according to the following procedure. GML and lauryl acetate were mixed in a polysiloxane adhesive solution (XT-4502, Dow Corning). In a separate step, polyvinyl pyrrolidone (PVP) (Povidone, ISP Van Dyk, Bellevue, N.J.) was dissolved in ethanol. Testosterone was then added to the ethanol/PVP solution and the resultant solution was mixed for approximately one hour. This solution was then added to the GML/lauryl acetate/polysiloxane solution. The resulting solution was heated to approximately 50° C. and mixed for a few hours until a fine white dispersion was obtained. The dispersion was then cast onto a backing (CoTrans 9720, 3M) to a wet thickness of about 10–17 mils. The solution was then heated in a drying oven at 70° C. for approximately one hour. The resulting cast was 3–5 mils thick and was laminated to a release liner (FDC/PET 3M-1022). 2.5 cm² circular pieces were then die cut and used in the in vitro skin flux experiments according to Example 1. The compositions of the formulations made according to this procedure are shown in Table 5. Each of the formulations contained testosterone at a concentration in the matrix in excess of saturation.

TABLE 5

Matrix Composition (weight percent)

| FORMULATION | WEIGHT PERCENT |
| --- | --- |
| GML/lauryl acetate/testosterone/polysiloxane | 10/10/2/78 |
| GML/lauryl acetate/PVP/testosterone/polysiloxane | 10/10/10/2/68 |
| GML/lauryl acetate/PVP/testosterone/polysiloxane | 2/10/10/2/76 |
| testosterone/EVA 40 | 2/98 |

Figure 9:
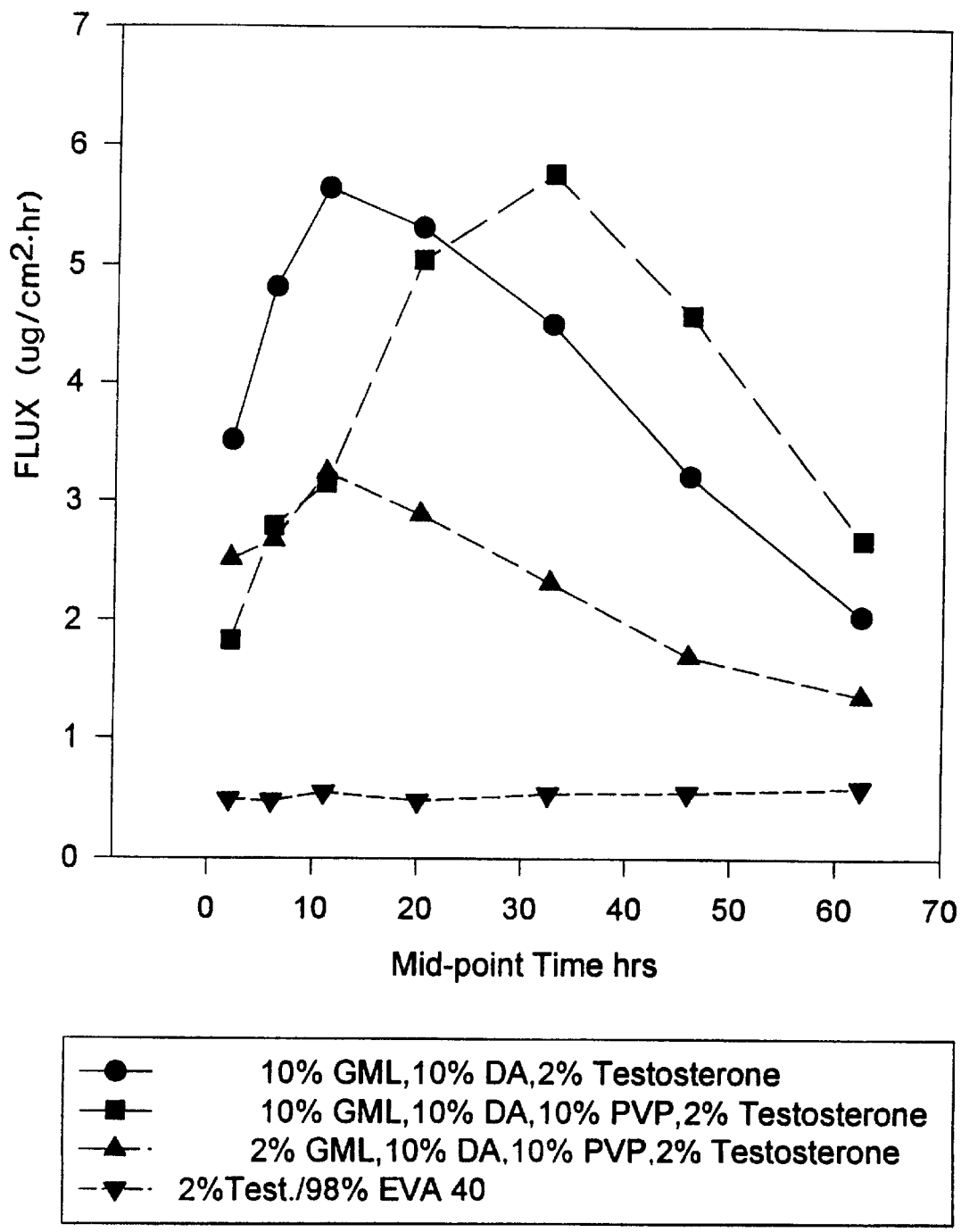
FIG. 9 is a graph of the flux of testosterone through human epidermis at 35° C. using various formulations of GML with lauryl acetate.

The skin flux experiment described in Example 1 was repeated for these systems, substituting 0.1% phenol as the receptor solution. The effect of the concentration of GML and lauryl acetate on the flux of testosterone through human epidermis from matrix systems at 35° C. is shown in FIG. 9. As seen in FIG. 9, formulations including GML and lauryl acetate resulted in a 4–10 fold increase in flux over the EVA 40 control without enhancers.

The invention has been described in detail with particular reference to certain preferred embodiments thereof, but it will be understood that variations and modifications can be affected within the scope and spirit of the invention.

What is claimed is:

1. A pressure sensitive adhesive composition for the transdermal administration of a therapeutic agent comprising, by weight:
    (a) 0.1–30% of a therapeutic agent,
    (b) 30–90% of a hydrophobic pressure sensitive adhesive,
    (c) 1–40% of a permeation enhancer capable of plasticizing the hydrophobic pressure sensitive adhesive, said permeation enhancer comprising lauryl acetate and a monoglyceride.

2. A composition according to claim 1 wherein the composition is a hot melt pressure sensitive adhesive.

3. A composition according to claim 2 comprising a viscosity within the range of $10^3$–$10^7$ Poise.

4. A composition according to claim 3 comprising a viscosity within the range of $2\times10^5$–$10^6$ Poise.

5. A composition according to claim 1 wherein the composition comprises 1–30% glycerol monolaurate and 1–30% by weight lauryl acetate.

6. A composition according to claim 1 further comprising 1–30% by weight of a water absorbing polymer.

7. A composition according to claim 6 wherein the water absorbing polymer is selected from the group consisting of polyvinyl pyrrolidone, polyvinyl alcohol, and polyaminoacrylates.

8. A device for the transdermal administration of a therapeutic agent at a therapeutically effective rate comprising:
   (a) a backing layer, and
   (b) an agent reservoir matrix on the skin contacting surface of the backing layer comprising a polymeric blend comprising, by weight:
      (i) 40–90% of a hydrophobic pressure sensitive adhesive,
      (ii) 0.1–30% therapeutic agent, and
      (iii) a permeation enhancer comprising 1–30% of a monoglyceride and 1–30% lauryl acetate.

9. A device according to claim 8, wherein the monoglyceride is glycerol monolaurate.

10. A device according to claim 8 wherein the agent reservoir further comprises 1–30% of a water absorbing polymer.

11. A device according to claim 10 wherein the water absorbing polymer is selected from the group consisting of polyvinyl pyrrolidone, polyvinyl alcohol, and polyaminoacrylates.

12. A device according to claim 11 wherein the water absorbing polymer is polyvinyl pyrrolidone.

13. A device according to claim 11 wherein the hydrophobic pressure sensitive adhesive is a polysiloxane adhesive.

14. A device according to claim 9 wherein the therapeutic agent is selected from the group consisting of testosterone, progesterone, nandrolone, and estradiol.

15. A device according to claim 14 wherein the therapeutic agent is testosterone.

16. A device according to claim 15 wherein the reservoir matrix comprises testosterone at or above saturation.

17. A device according to claim 10 comprising 60–90% polysiloxane adhesive, 5–25% polyvinyl pyrrolidone, 1–15% testosterone, 1–20% glycerol monolaurate, and 1–20% lauryl acetate.

18. A device according to claim 8 wherein the lauryl acetate is at least 97% pure.

19. A composition according to claim 1 wherein the hydrophobic pressure sensitive adhesive comprises a polysiloxane adhesive.

* * * * *